(12) United States Patent
Koppes et al.

(10) Patent No.: US 7,399,841 B1
(45) Date of Patent: Jul. 15, 2008

(54) HIGH-ENERGY 1,3,5-TRIAZINYL DIAZENES, AND PROCESS THEREOF

(75) Inventors: William M. Koppes, Adelphi, MD (US); Farhrad Forohar, LaPlata, MD (US); Jesse Moran, King George, VA (US); David M. Rosenberg, Bryans Road, MD (US); Joseph D. Mannion, Washington, DC (US); Brian W. Vos, Sliver Spring, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 11/229,429

(22) Filed: Sep. 15, 2005

(51) Int. Cl.
*C07D 403/12* (2006.01)
*C06B 43/00* (2006.01)

(52) U.S. Cl. .................. 534/556; 534/567; 534/586; 534/767; 149/36

(58) Field of Classification Search ............ 534/556, 534/567, 586, 767; 149/36
See application file for complete search history.

(56) References Cited

U.S. PATENT DOCUMENTS

| | | | |
|---|---|---|---|
| 1,625,531 A | 4/1927 | Fritzsche et al. | 544/208 |
| 2,320,819 A | 6/1943 | D'Alelio | 528/253 |
| 2,827,451 A | 3/1958 | Towne et al. | 534/767 |
| 2,884,383 A | 4/1959 | Grundmann et al. | 528/423 |
| 3,149,100 A | 9/1964 | Hindermann et al. | 534/634 |
| 3,309,345 A | 3/1967 | Lutwack | 528/390 |
| 3,983,115 A | 9/1976 | Seitz et al. | 544/212 |
| 4,082,739 A | 4/1978 | Seitz | 534/634 |
| 4,985,539 A | 1/1991 | Fornasier et al. | 538/423 |
| 5,099,017 A | 3/1992 | Eberspach et al. | 544/198 |
| 6,197,957 B1 | 3/2001 | Forgione et al. | 544/198 |
| 6,342,589 B1 | 1/2002 | Hiskey et al. | 534/567 |
| 7,119,179 B1 * | 10/2006 | Huynh et al. | 534/767 |

OTHER PUBLICATIONS

Loew et al., J. Heterocyclic Chem., 13, 829-833, 1976.*
Huynh et al., Angew. Chem. Int. Ed., 43(37), 4924-4928, 2004.*

* cited by examiner

*Primary Examiner*—Fiona T Powers
(74) *Attorney, Agent, or Firm*—Fredric J. Zimmerman

(57) ABSTRACT

A compound possesses the chemical structure of:

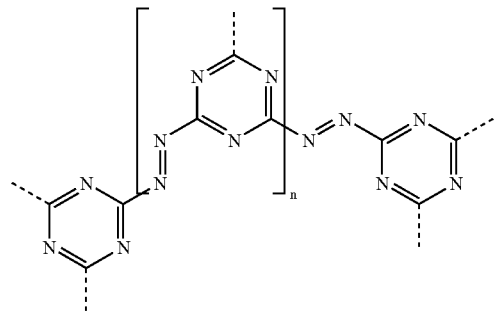

wherein n is greater than zero. The compound is useful in energetic composition, particularly in linear, branched, dendritic, oligomer and cyclic oligomer azo-triazine forms.

18 Claims, 11 Drawing Sheets

HIGH-ENERGY 1,3,5-TRIAZINYL DIAZENES, AND PROCESS THEREOF

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The present invention provides novel high-nitrogen energetic compounds. More particularly these compounds include extended systems of hydrazo and azo-linked, 1,3,5-triazines, and the preparation thereof, that are particularly applicable as ingredients in propellant formulations and other energetic formulations.

BACKGROUND

Propellant formulations for rocket motors have limitations in that the goal of higher performance must be balanced with the concomitant decrease in stability and safety properties associated with performance gains. High performance propellant compositions may exhibit an undesirable pressure exponent during combustion that can lead to motor failure. The mechanical properties of the propellant grain are also important to optimum performance. Bonding characteristics between the binder and the other propellant ingredients is a factor in achieving improved mechanical properties of the propellant.

Single azo-triazine structures have been disclosed in P. Loew and C. D. Weis, J. Heterocyclic Chem., 1976, 13, 829, the disclosure of which is herein incorporated by reference. However, Loew et al. does not disclose any extended systems of these single azo-triazine structures.

There is a need in the art to provide improved energetic materials. The present invention addresses this and other needs. In particular, the present invention provides novel high-nitrogen energetic compounds. These compounds include extended networks of hydrazo and azo-linked, 1,3,5-triazines, and the preparation of dendrimers and cyclic oligomers of the 4,6-substituted triazines, wherein the substituents are energetic groups. An unexpected result is that these triazine networks provide for planar arrays of energetic compositions that maximize density and insensitivity properties, important for their application as propellant ingredients.

SUMMARY OF THE INVENTION

The present invention includes compounds possessing the chemical structure of:

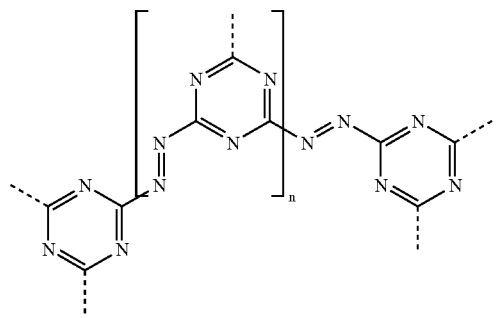

wherein n is greater than zero. The chemical structures of the present invention are particularly suitable for forming linear, branched, dendritric, oligomer and cyclic oligomer azo-triazine forms.

The present invention also includes a process for producing azo-triazine compounds, comprising providing a N,N'-Bis-(4,6-substituted-[1,3,5]triazin-2-yl)-hydrazine, forming the diazene form thereof and extending the formed diazene.

DETAILED DESCRIPTION

Figure 1:
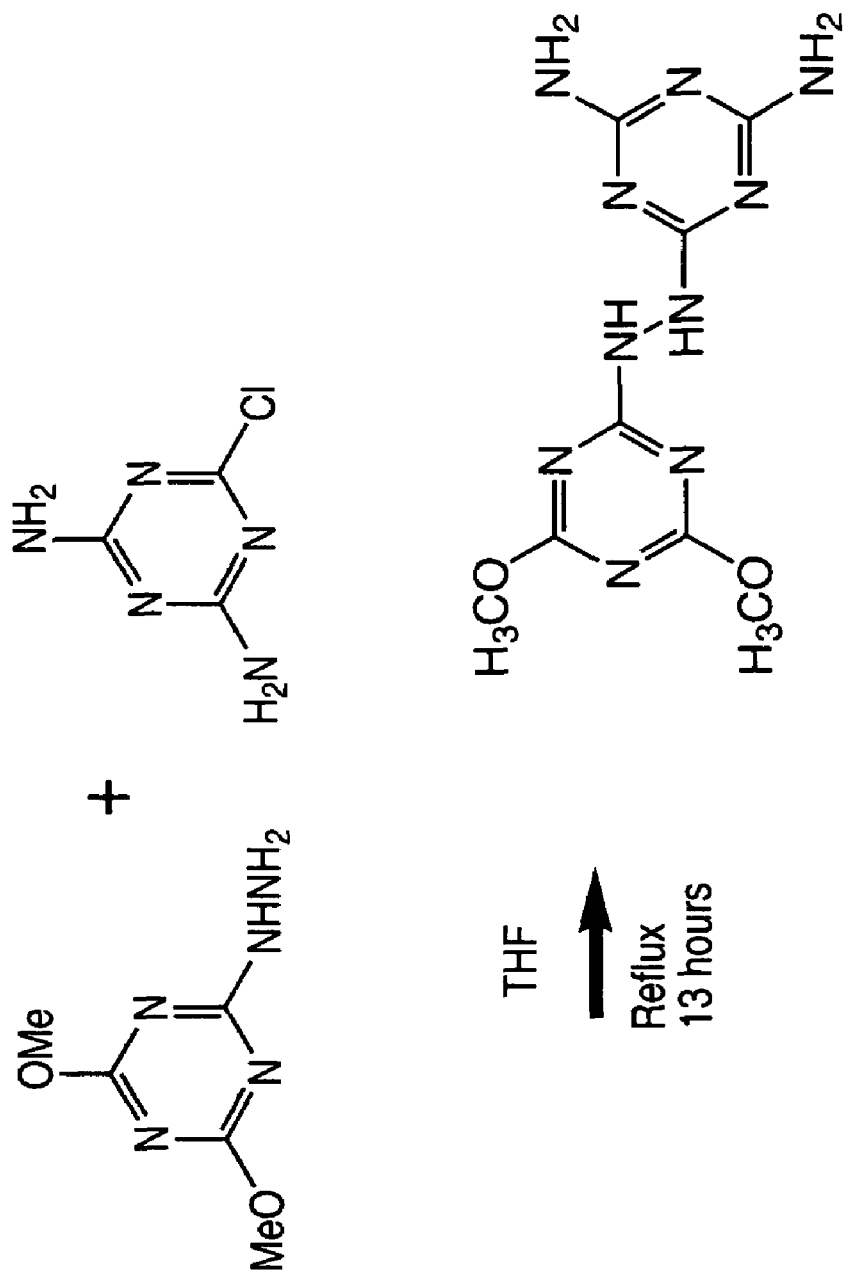
FIG. 1 illustrates one method of forming a precursor for the present invention.

The present invention provides novel extended system azo-linked 1,3,5-triazines, and the preparation thereof, that are particularly applicable as ingredients in propellant formulations and other energetic formulations. The present invention provides methods to form the triazine monomers for particular growth patterns, such as forming the hydrazo linkage for conversion to an azo linkage. The oligomer size is increased, as desired, to achieve specific properties. Additional modifications of the structures, and pendent groups (also referred to herein as termini or substituents), optimize physical properties while making higher-energy CHNO compounds. Due to the azo bond, the structures of the present invention are generally planar having high density and enhanced stability resulting from a layered structure. The structures may be synthesized in a stepwise method or by a one-step condensation reaction. With controlled coupling of the triazine rings, a series of products with increasing molecular weight may be formed having various density, stability, and combustion properties (measurable, for example, by closed bomb apparatus measurements of dP/dt and dT/dt). Products resulting from one-step condensation reactions have the advantage of potential low-cost synthesis. A large variety of structures are possible, as the network of coupled rings can be formed through 1,3-couplings of the six-membered rings to give linear structures, or through 1,3,5-couplings to give dendritic structures.

The novel azo-linked 1,3,5-triazines of the present invention include the chemical structure of:

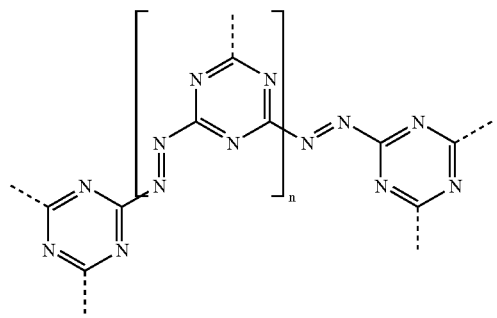

Structure A wherein n is greater than zero.

As seen in the Structure A, a 1,3,5-triazine has at least one azo coupling immediately adjacent one of the carbon atoms within the triazine ring. In an embodiment, Structure A includes a value of n ranging from about 1 or greater, such as, from about 1 to about 1000, 1 to 50, 50 to 500, etc. with value of n being determinable by specific physical and chemical properties desired, such as, nanosizing, layer distances, application methods, and other like factors that facilitate the manufacture of the chemical compositions for performance characteristics.

In one embodiment of the present invention, the compound includes a chemical structure of:

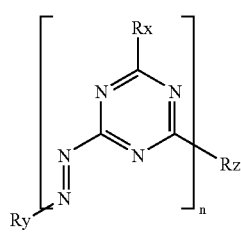

Structure B

Suitable Rx, Ry and Rz units include both energetic and non-energetic components, in cyclic and non-cyclic forms. In an embodiment, Ry possesses the chemical structure of:

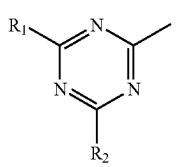

and Rz possesses the chemical structure of:

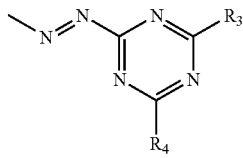

with at least one of Rx, $R_1$, $R_2$, $R_3$ and $R_4$, individually, being a leaving group, such as, cyclic and/or non-cyclic components, energetic and/or non-energetic substituents, and the like. In an embodiment, at least one of Rx, $R_1$, $R_2$, $R_3$ and $R_4$, individually, includes an energetic substituent, with most or all of the Rx, $R_1$, $R_2$, $R_3$ and $R_4$ being energetic substituents. Representative energetic substituents include, for example, without limitation, $NC(NH_2)(HNNH_2)$, NH, $NH_2$, $NHNH_2$ and $NC(NH_2)_2$, and in particular $NC(NH_2)_2$ and/or $NHNH_2$. Other energetic substituents include oxygenated nitrogen components including, for example, N-oxides generated from the triazine ring nitrogens and conversion of the azo-linkages to azoxy bonds.

As shown below, the methods of forming azo-linked triazine systems include the coupling of 2-chloro-4,6-disubstituted-1,3,5-triazines with a half-mole of hydrazine (Method A) and the reaction of a 2-hydrazino-4,6-disubstituted triazine with a 2-chloro-4,6-disubstituted-1,3,5-triazine (Method B). These hydrazo-linked compounds are then oxidized (Method C) to the triazinyl diazene products. High-nitrogen compounds, such as those useful in propellant applications, are made by substitution reactions on these triazinyl hydrazo and diazene products. Extension of these materials to an extended network of linked triazines provides a stable, dense, energetic structure. Such extended networks include a central triazine ring that is linked to other triazines. The 1,3,5-triazine structures of the present invention are particularly applicable for forming linear, branched, dendritric, oligomer, cyclic oligomer azo-triazine structures, including combinations and derivatives thereof. These complex structures allow high-energy compositions with increased stability. Energetic materials that incorporate the chemical compounds of the present invention have increased stability, with representative energetic materials including, for example without limitation, propellants, pyrotechnics, high energy detonators, and the like, and in particular, propellants. Linear azo-triazine compounds of the present invention include those compounds generally extending in two directions in a plane, with branched azo-triazine compounds of the present invention extending in three directions in a plane, and dendritric azo-triazine compounds of the present invention forming "tree-like" configurations. Polymeric, oligomer and cyclic oligomer azo-triazine compounds of the present invention include both macro- and limited unit structures.

EXAMPLES

Figure 4A:
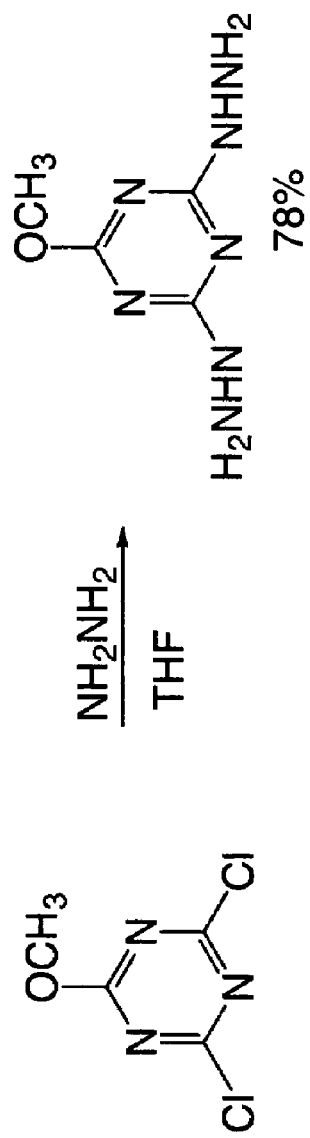
FIGS. 4A and 4B illustrate an example of forming a linear chemical structure of the present invention.
Figure 4A:
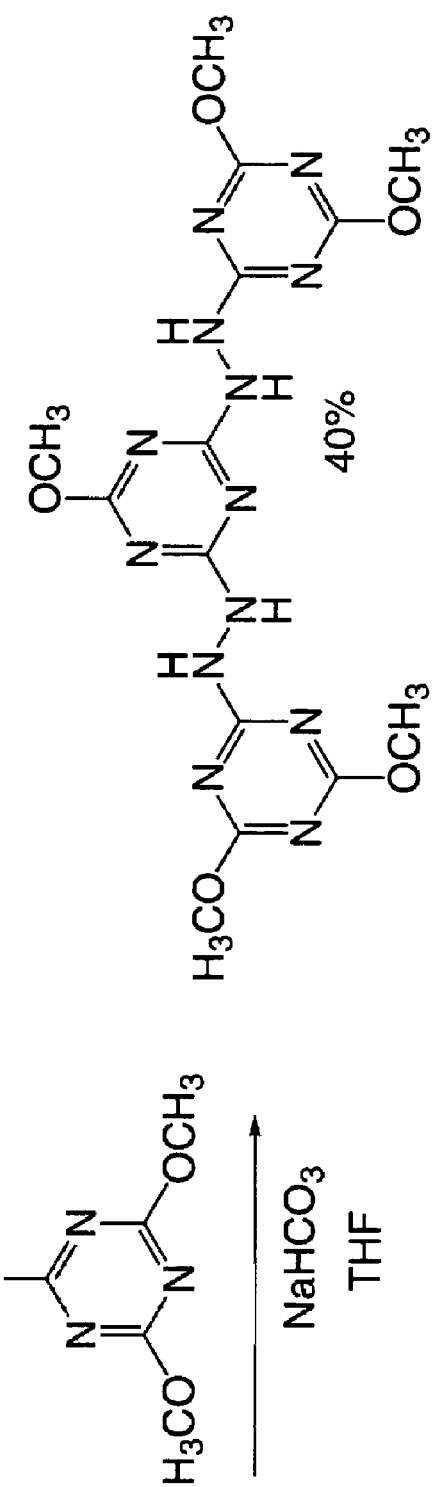
Figure 4B:
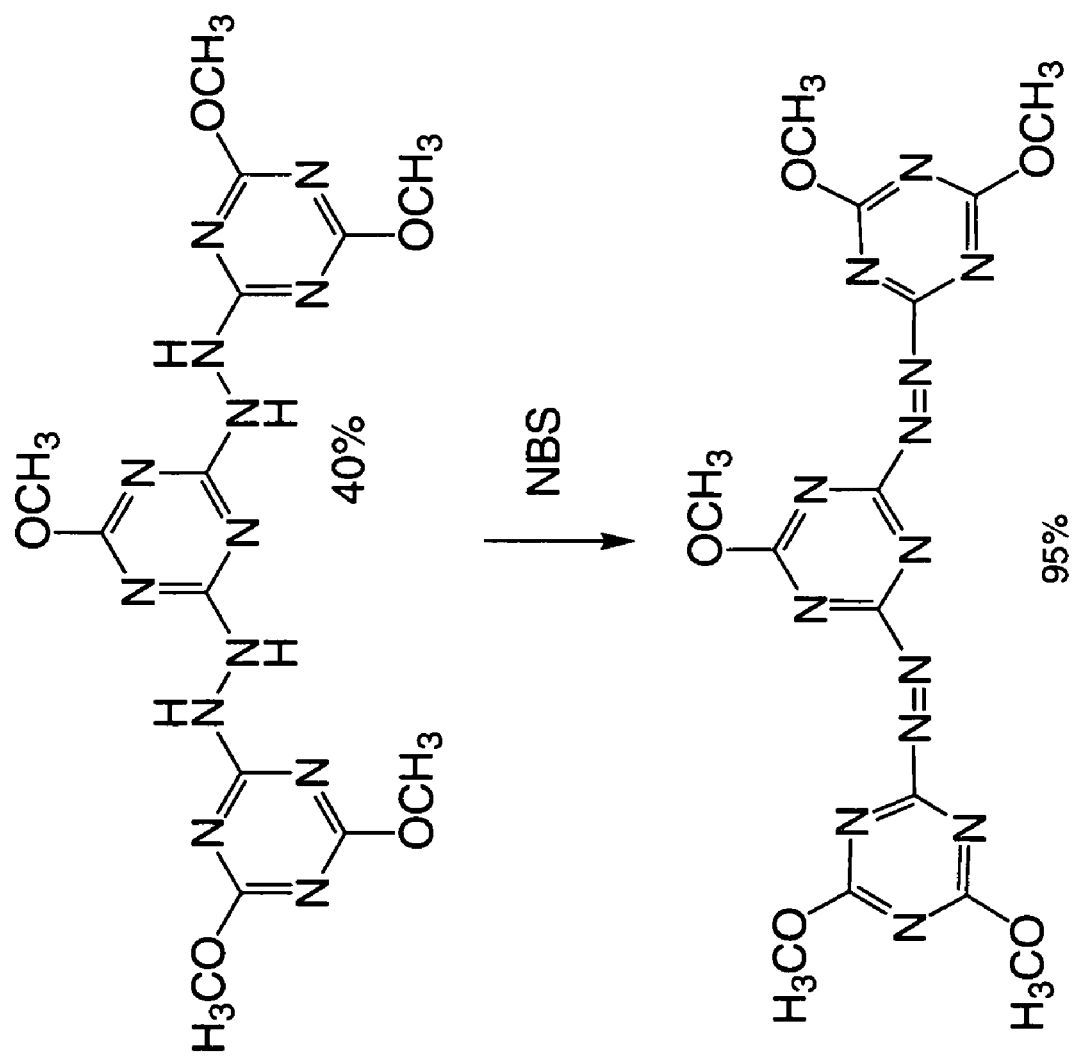

As seen in the examples, below, the process for producing extended system azo-triazine compounds of the present invention may include the steps of providing a N,N'-Bis-(4,6-substituted-[1,3,5]triazin-2-yl)-hydrazine, forming the diazene form of the hydrazine and extending the formed diazene. Formation of the N,N'-Bis-(4,6-substituted-[1,3,5]triazin-2-yl)-hydrazine may be accomplished as shown in Examples 1a-1d, below, with FIG. 1 exemplified in Example 1d, and FIG. 2 exemplified in Example 3b. Additionally, FIGS. 4A, and 4B are exemplified in Examples 7, and 8, respectively.

A. Precursor

Example 1a

Formation of N,N'-Bis-(4,6-dimethoxy-1,3,5-triazin-2-yl)-hydrazine

Hydrazine monohydrate (1.72 g, 34.4 mmol) was added slowly to a solution containing chloro-dimethoxy-triazine (12.1 g, 68.9 mmol.), $K_2CO_3$ (9.52 g, 68.9 mmol.), and 100 mL of isopropanol. After several hours at 50° C., the initially white, opaque mixture turned slightly pink. The mixture was stirred and heated overnight. A light-pink solid was isolated by filtration and a water wash. After oven drying, a white solid product was obtained (10.6 g, 99%): mp 222-4° C., $^1$H-NMR ($d_6$-DMSO): 9.751 (N—H, 2H) 3.855, 3.764 (—$OCH_3$, 12H), ($CDCl_3$): 7.45 (N—H, 2H) 3.95, 3.91 (—$OCH_3$, 12H), $^{13}$C-NMR ($d_6$-DMSO): 172.2, 171.7 (—C-OMe) 169.5 (C—NHNH), 54.4, 54.2 (—$OCH_3$). (see P. Loew and C. D. Weis, J. Heterocyclic Chem., 1976, 13, 829).

Example 1b

Preparation of N,N'-Bis-(4,6-dichloro-[1,3,5]triazin-2-yl)-hydrazine

Note: Contact of the hydrazine reagent with metal prior to its addition to the reaction solution can cause unwanted oligomerization reactions. A suspension of cyanuric chloride (18.4 g, 100 mmol) in THF (100 ml) was cooled to −15° C. A solution of hydrazine monohydrate (7.51 g, 150 mmol) in water (10.0 mL) was added dropwise to the stirred cyanuric chloride suspension over 5 min, and the reaction mixture was then stirred at 0° C. for 30 min.

Cold water (4° C., 100 mL) was added to the reaction mixture, and after the oil was allowed to separate (ca. 5 min), the aqueous layer was decanted. After two more aqueous washings and decantations with cold water, warm water was added (40° C., 100 mL) and the reaction mixture was allowed to sit for 5 min. The remaining yellow solid was vacuum filtered using a Whatman #1 filter, and then washed with water (RT, 4×25 mL) and $CHCl_3$ (2×25 mL). The yellow powder was dissolved in acetone (100 mL), dried with magnesium sulfate, and then the solvent was removed via rotary evaporation from a room temperature water bath. The yellow solid was stored immediately at −20° C. (13.6 g, 83%). (The impure product readily undergoes oligomerization at room temperature in a few hours, either as the acetone solution or as the solid. Although some oligomerization occurs after a week at −20° C., the insoluble oligomer is easily separated from an acetone solution by filtration.) Flash-column chromatography on silica gel (3:1 petroleum ether-EtOAc; $R_f$ 0.45) of the dry-loaded material yielded the pure, white solid (10.2 g, 62%) that did not undergo oligomerization at room temperature. $^1$H NMR ($d_6$-Acetone) δ10.32 (s). $^{13}$C NMR ($d_6$-Acetone) δ172.2, 171.3, and 168.7. IR (ATR): 3225, 3095, 2960, 1600, 1560, 1530, 1505, 1425, 1385, 1300, 1265, 1245, 1215, 1190, 1005, 860, 800, 750, and 700 cm$^1$. mp>250° C.

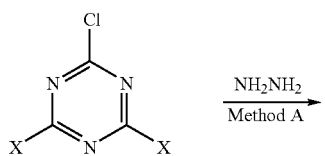

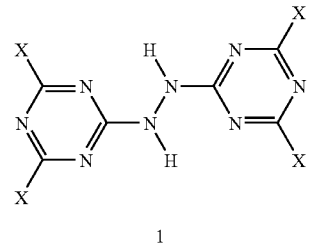

X = $OCH_3$, 1a; Cl, 1b

Examples 1a and 1b

Example 1c

Prep. of N,N'-Bis-(4,6-dimethoxy-[1,3,5]triazin-2-yl)-hydrazine (1a)

To 0.5 g (1.5 mmol) of 1b in 1.2 ml of methanol was added 1.2 ml of a 5.4M methanol solution of sodium methoxide (7.0 mmol). A yellow suspension formed, and was stirred at room temperature for about 48 hours. The suspension was then concentrated by rotary evaporation to obtain a solid. Evaporation of an acetone extract of this material gave the product 1a, which was identical to the product produced in the chlorodimethoxytriazine reaction with hydrazine in Method A.

Example 1d

Preparation of 6-[N'-(4,6-Dimethoxy-[1,3,5]triazin-2-yl)-hydrazino]-[1,3,5]triazine-2,4-diamine A mixture of dimethoxy triazinyl hydrazine (0.986 g, 5.76 mmol.) and chlorodiaminotriazine (0.858 g, 5.89 mmol.) was refluxed in 15 mL of THF for 13 hours. The crude product was filtered, washed with 20 mL of dichloroethane, and extracted with 50 mL of EtOH. Un-dissolved solid was removed by filtration, and the filtrate was concentrated by evaporation to give 0.216 g (13%) of the product: mp (sintered without melting, up to 400° C.); $^1$H-NMR ($d_6$-DMSO) 9.94 (2.3H), 7.77 (4.5H, broad), 3.86, 3.79 (6.0H)

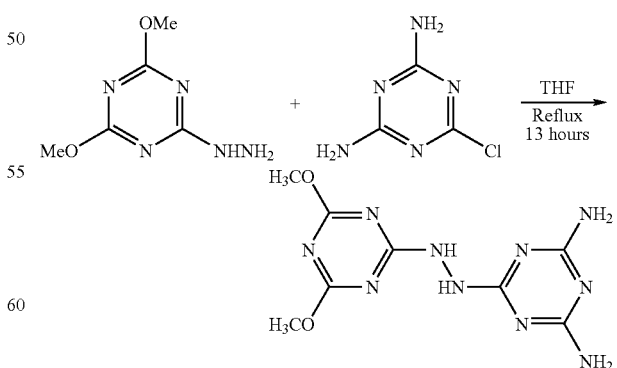

The reagents corresponding to the interchange of the hydrazine and chlorine groups between the triazines may also accomplish the synthesis.

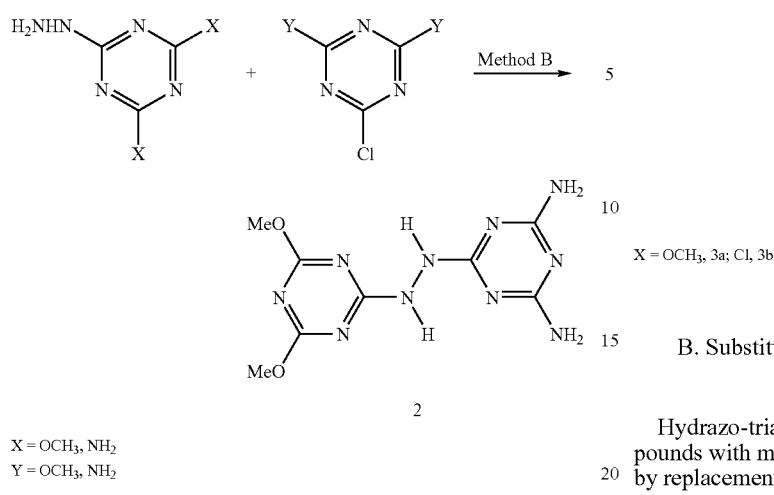

Example 3

Preparation of Bis-(4,6-substituted-[1,3,5]triazin-2-yl)-diazene

Example 3a

Preparation of Bis-(4,6-dimethoxy-[1,3,5]triazin-2-yl)-diazene

The product of Example 1a (7.4 g. 23.8 mmol) was added slowly to a stirred mixture of 20.4 g. (115 mmol) of N-bromosuccinimide and 80 mL of acetonitrile at ambient temperature. A dark orange solution formed after 2 h of stirring. A brown/orange powder was isolated by filtration. After a water-wash, the solid was dried in a desiccator to give 5.7 g (77%) of crude product. Recrystallization from acetic acid gave brick-red needles: mp 228-232° C. (dec); $^1$H-NMR (d$_6$-DMSO): δ4.060 (—OCH$_3$); (CDCl$_3$) δ(—OCH$_3$); $^{13}$C-NMR (CDCl$_3$) δ(—OCH$_3$), 173.8 (C-OMe), 176.4 (C—N=N). Anal. Cacld for C$_{10}$H$_{12}$N$_8$: C, 38.96; H, 3.92; N, 36.35. Found: C, 38.78; H, 3.94; N, 36.02.

Example 3b

Preparation of Bis-(4,6-dichloro-[1,3,5]triazin-2-yl)-diazene

Figure 2:
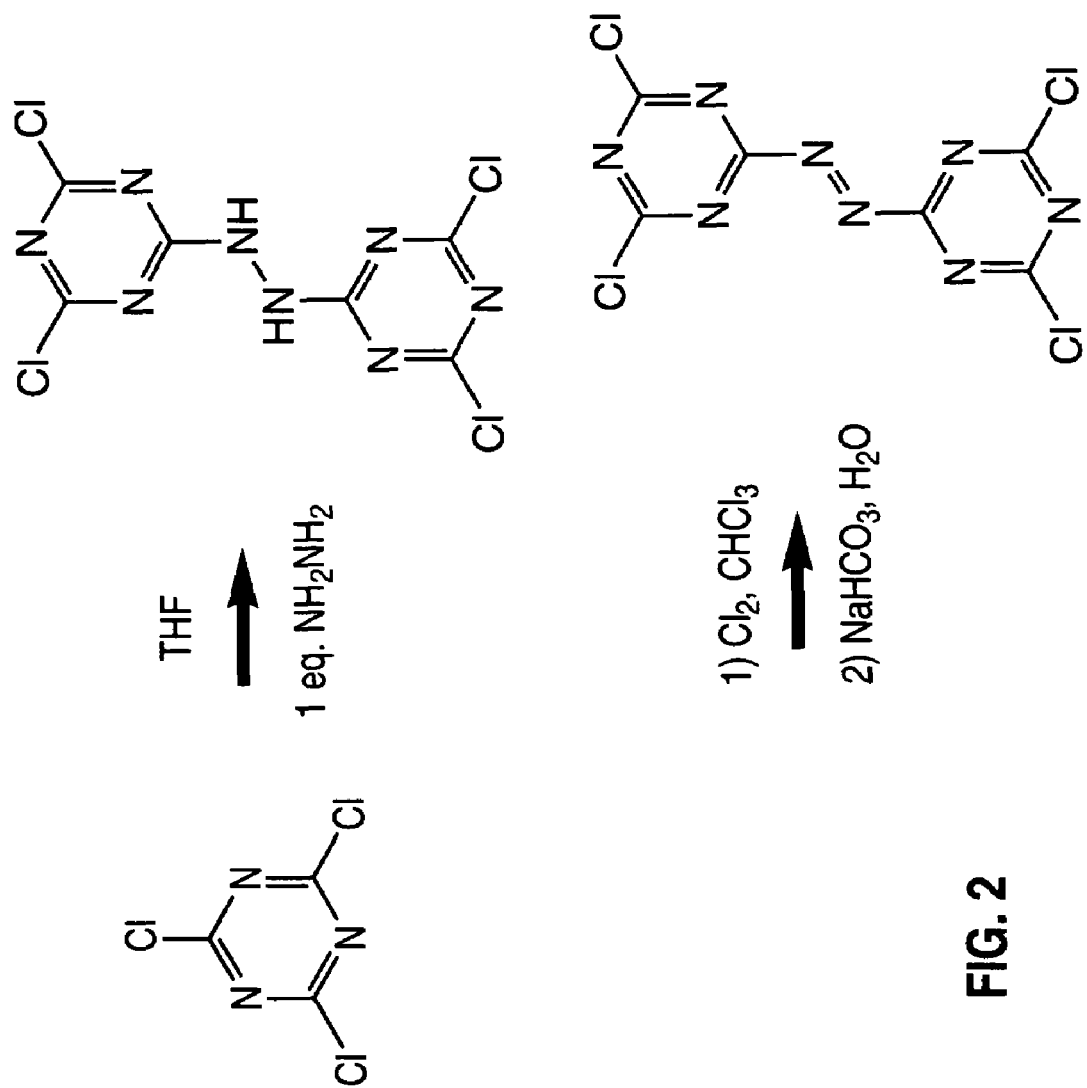
FIG. 2 illustrates a second method of forming a precursor for the present invention.

As seen in FIG. 2, and below, the product of Example 1b was oxidized with chlorine to the diazene 3b in a two-phase system of a suspension of 1b in chloroform

B. Substitution Reactions of Triazinyl Diazene and Hydrazo Compounds

Hydrazo-triazine compounds and azo-linked triazine compounds with methoxy and chloro substituents were modified by replacement of these groups, shown in Example 4, below.

Example 4

Preparation of N,N'-Bis-(4,6-dihydrazino-[1,3,5]triazin-2-yl)-hydrazine

A 15.88 g (317 mmol) quantity of hydrazine monohydrate was added to a stirred suspension of 1.63 g (5.3 mmol) of 3a in 22 mL of water. Gas evolution was observed for a period of approximately a half-hour, during which the orange suspension turned colorless. A heating bath was set in place and a reflux was established in the mixture for a period of 3 h. The solution was cooled and the solid was filtered, washed with water, and extracted with hot DMSO. The oven-dried, residual solid sintered without melting, up to 400° C. Anal. Calcd for C$_6$H$_{14}$N$_{16}$: C, 23.23; H, 4.55; N, 72.73. Found: C, 2369; H, 4.93; N, 69.78.

Example 4

C. Azo-Coupling of Two Triazines to a Central Triazine

Example 5

Preparation of 2,4-Dichloro-6-methoxy-s-triazine

Cyanuric chloride was reacted with methanol in the presence of bicarbonate at 30° C. as described in the literature to give the product: mp 89-91° C. (lit mp 87-89° C., J. R. Dudley, et al, J. Amer. Chem. Soc., 1951, 73, 2986-2990), after recrystallization from heptane. $^1$H-NMR (CDCl$_3$): δ4.12 (OCH$_3$).

Example 6

Preparation of 2,4-Dihydrazino-6-methoxy-s-triazine

A mixture of the product of Example 5 (10.05 g, 55.56 mmol and THF (240 mL) was stirred vigorously for 5 min. Hydrazine monohydrate (11.4 g, 0.226 mol) was added in one portion at room temperature and this was allowed to stir for 1 hour, then refluxed with a heating mantle for an additional 4½ hrs. The solution was allowed to cool for 20 min. at room temperature, and placed in an ice bath. Water (120 mL) was added, and the solution was filtered, rinsed (H$_2$O), and dried in a vacuum desiccator to give 7.46 g (78% yield) of product: mp (sintering at approximately 200° C.); DSC, dec. max at 211° C.

Example 7

Preparation of 2,4-bis(hydrazo-2,4-dimethoxytriazinyl)-6-methoxy-s-triazine

Sodium bicarbonate (6.29 g, 74.8 mmol) was added with rapid stirring to a homogeneous solution of 2-chloro-4,6-dimethoxy-s-triazine (10 g, 56.1 mmol) in THF (128 mL), followed by the product of 6 (3.2 g, 18.7 mmol), in one portion. After 4½ hr of reflux, the solution was allowed to cool for 15 min, then filtered, rinsed (THF*30 ml, H$_2$O*60 ml), and the collected solid placed in a desiccator overnight. The crude product (2.8 g) was recrystallized in 125 mL of water. The filtered and dried product (1.70 g, 68% recovery, 20% yield) had the following properties: $^1$H-NMR (d$_6$-DMSO) 9.76 (m), 9.64 (m), 9.36 (m), 9.26 (s), 3.86-3.69 (m). (secondary coupling leads to a complicated spectrum.)

Example 8

Preparation of 2,4-bis(azo-2,4-dimethoxytriazinyl)-6-methoxy-s-triazine

A homogeneous solution of N-bromosuccinimide (3.16 g, 17.9 mmol) in 30 mL of CH$_3$CN (30 ml) was prepared at room temperature. The product of 7 (1.005 g, 2.23 mmol) was added to the well-stirred solution. The color of the solution changed from a white milky color, to light yellow, and finally deep orange in rapid succession. After 4 hr, the solution was filtered, and the solid product was washed with water. The dried material (0.94 g, 95%) was an orange powder with the following properties: $^1$H-NMR (CDCl$_3$) 4.29 (s, 3H); 4.15 (s, 12H); $^{13}$C-NMR (CDCl$_3$) 176.28, 175.71, 173.71, 173.46, 57.30, 56.35.

Anal. Calcd for C$_{14}$H$_{15}$N$_{13}$O$_5$: C, 37.76; H, 3.39; N, 40.89. Found: C, 37.69; H, 3.51; N, 40.31.

Figure 3:
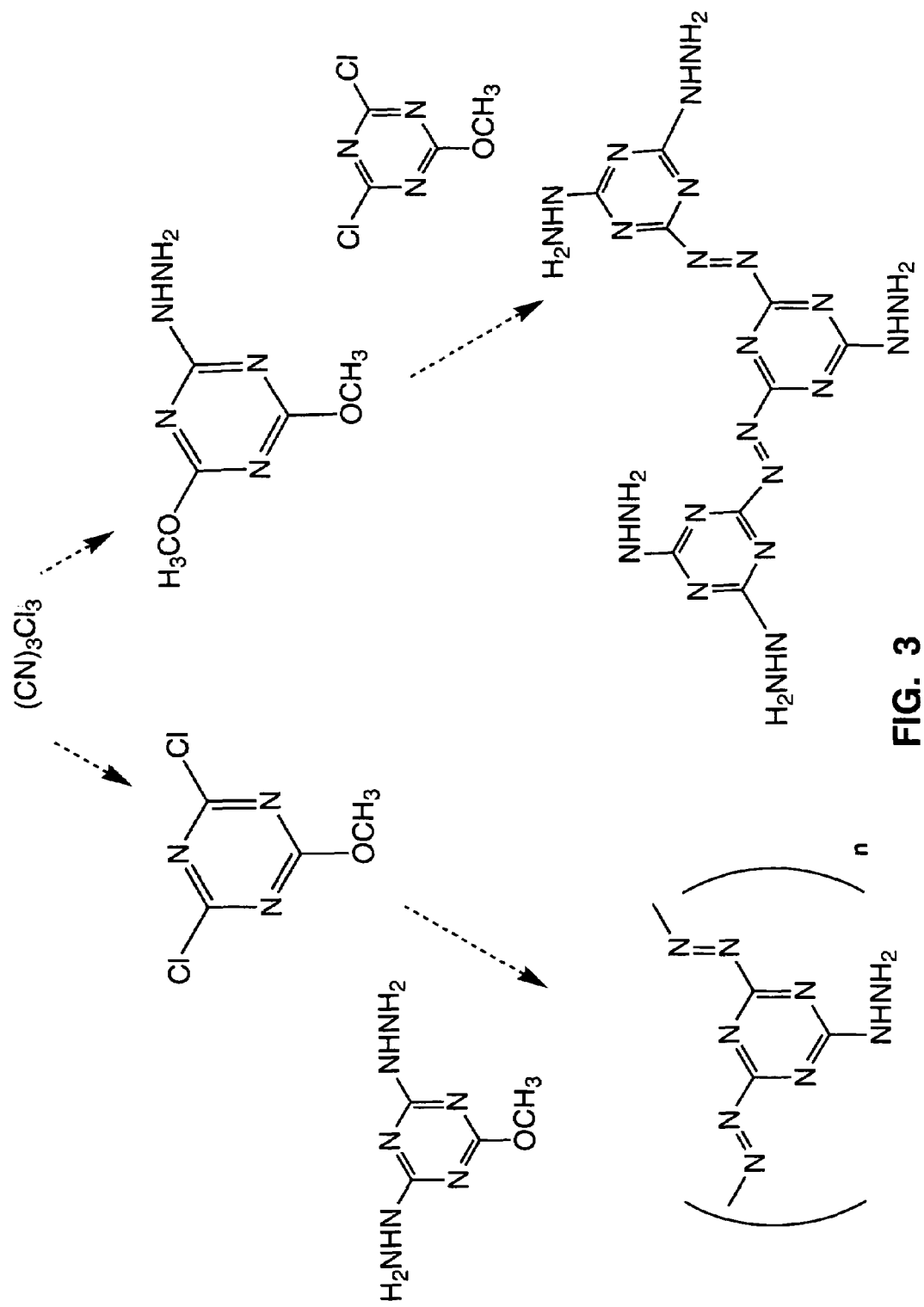
FIG. 3 illustrates two embodiments of the present invention forming a linear diazene from two different 1,3,5-triazine structures having polymer and oligomeric extended patterns.
Figure 5:
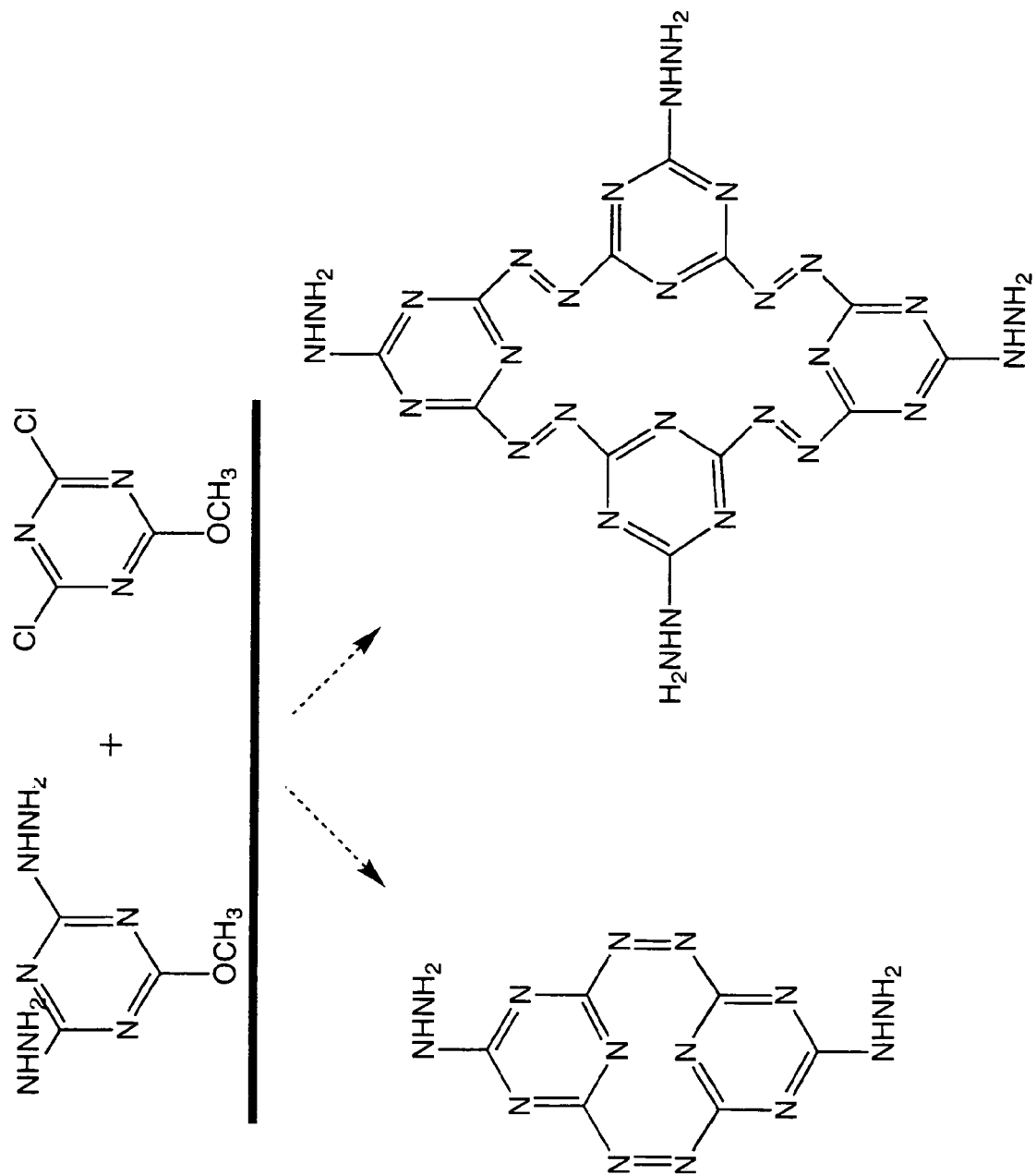
FIG. 5 illustrates formation of a cyclic oligomer chemical structure of the present invention.
Figure 6:
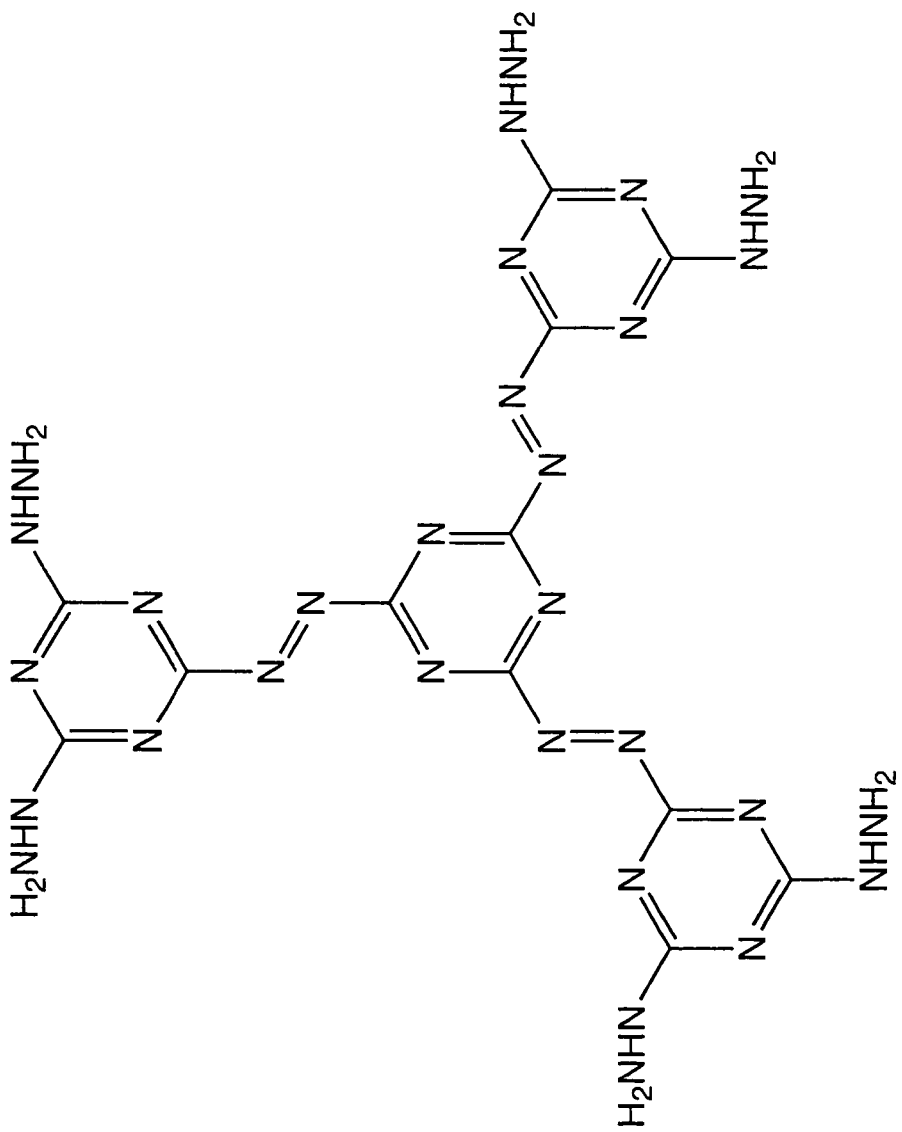
FIG. 6 illustrates a dendritic azo-triazine chemical structure of the present invention having hydrazine ($NHNH_2$) termini.
Figure 7:
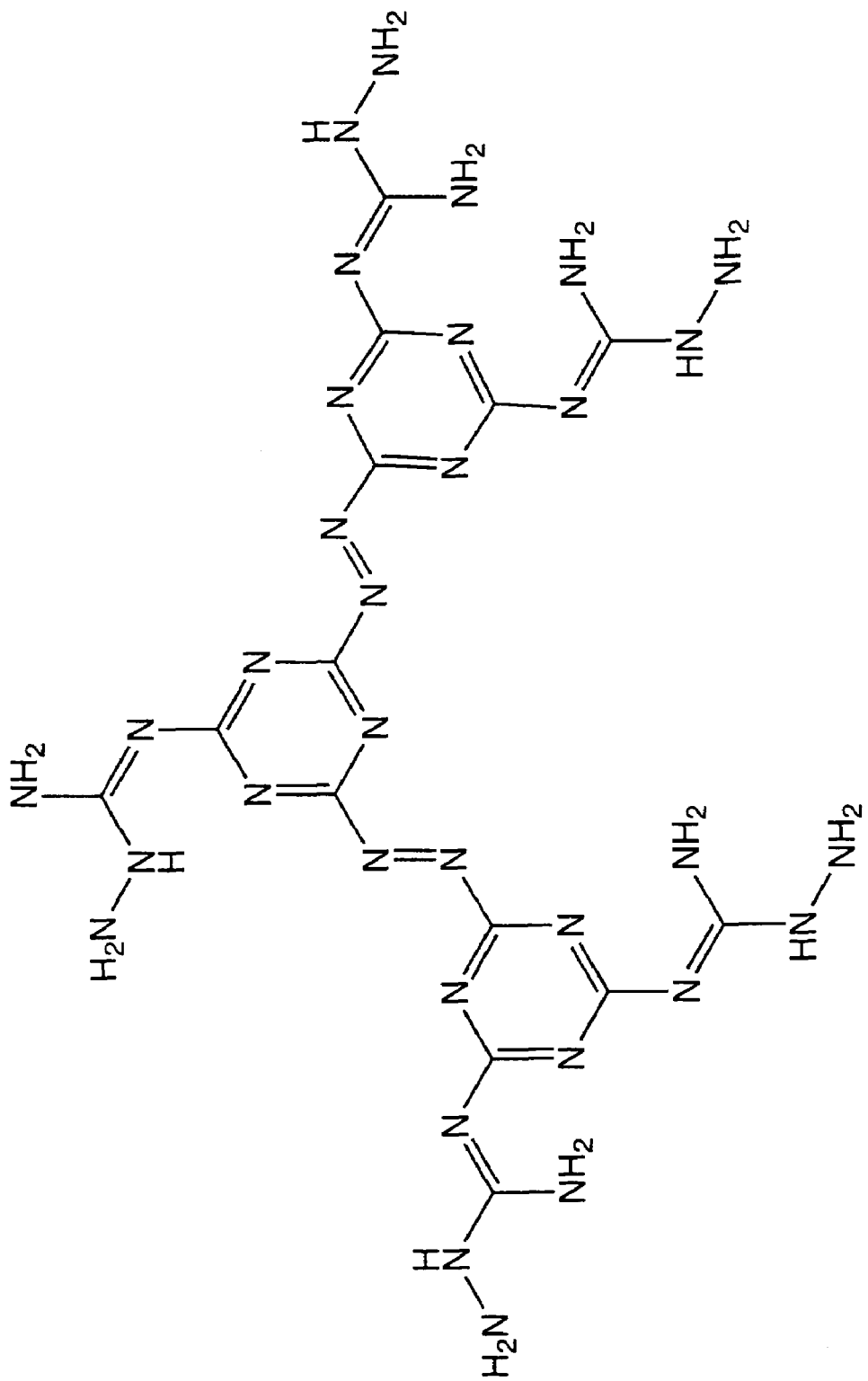
FIG. 7 illustrates a branched azo-triazine of the present invention having aminoguanyl ($NC(NH_2)(NHNH_2)$) termini.
Figure 8:
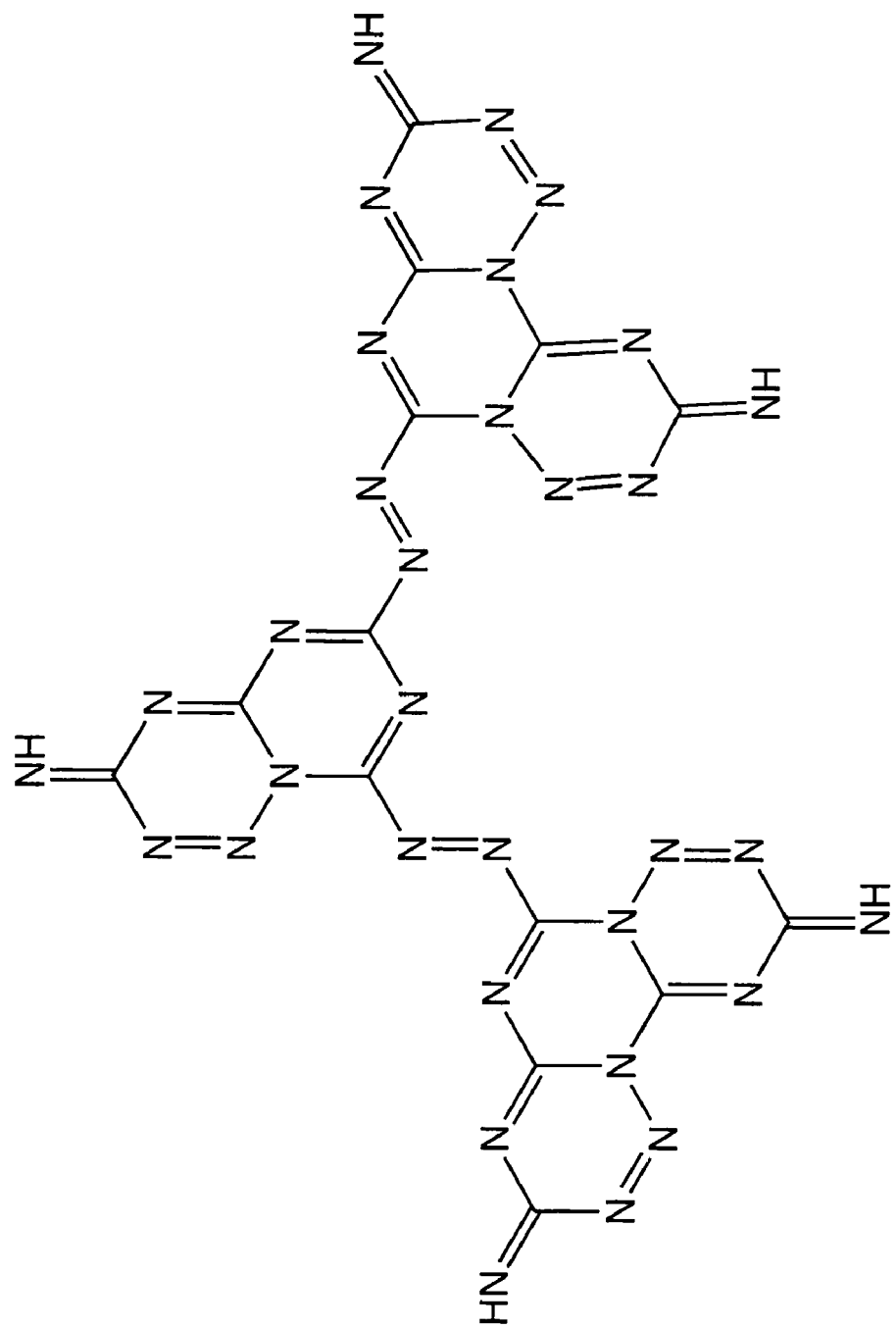
FIG. 8 illustrates a linear extended azo-triazine structure of the present invention with fused 1,2,3,5-tetrazinyl groups having =NH termini.
Figure 9:
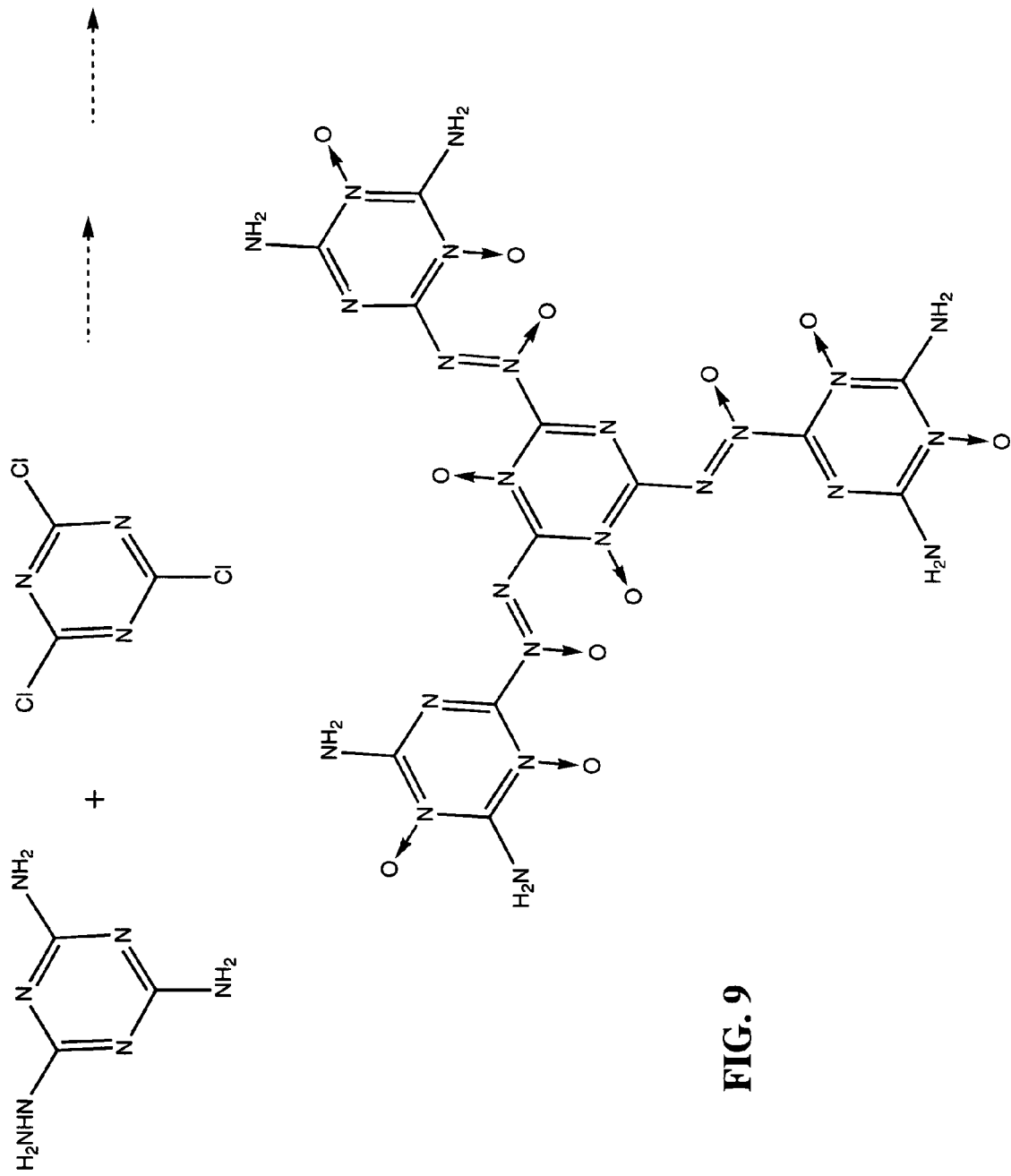
FIG. 9 illustrates formation of an N-oxide dendrimer structure of the present invention.
Figure 10:
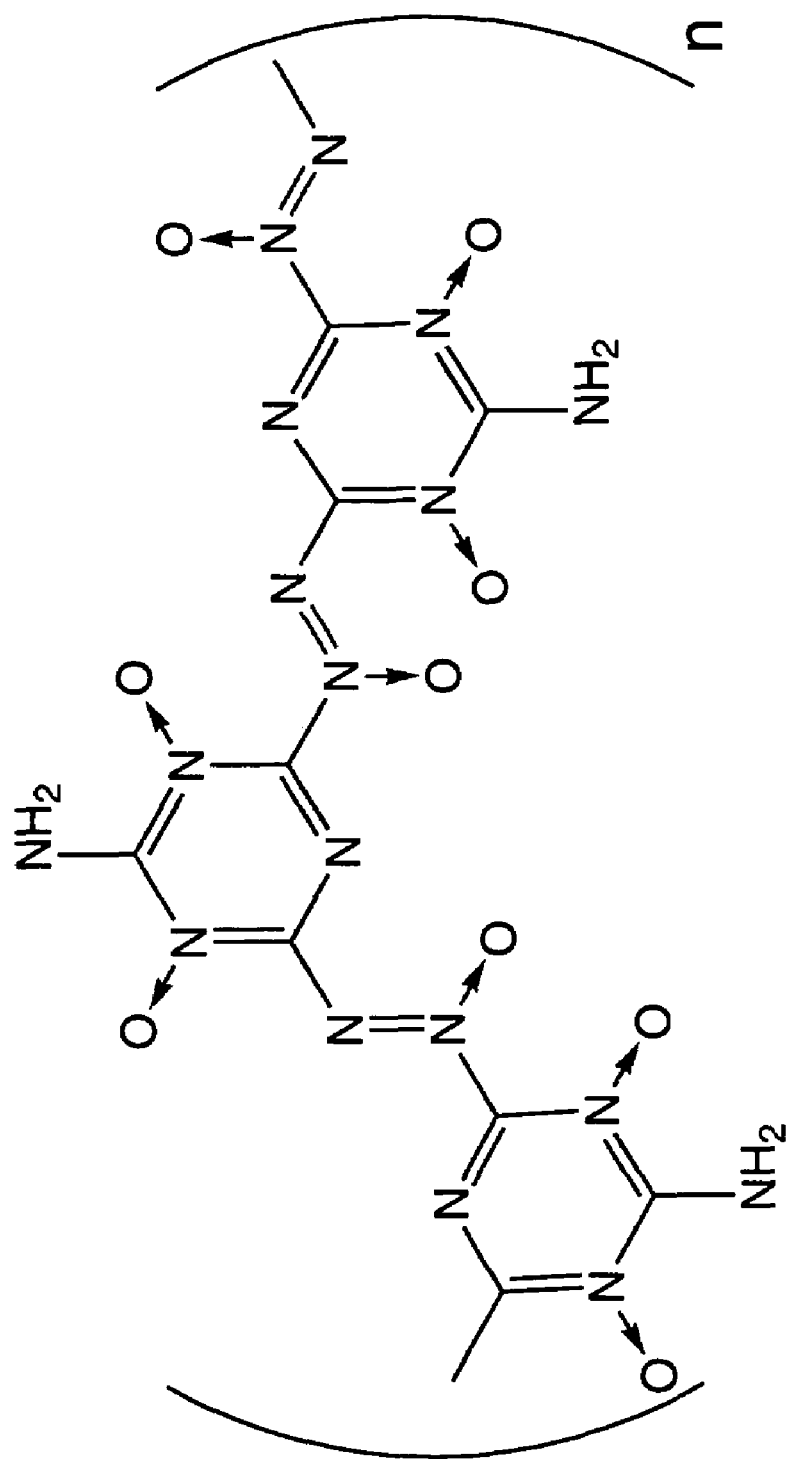
FIG. 10 illustrates an extended polymeric system of the present invention with N-oxide components.

As seen in FIGS. 3-10, several extended triazinyl diazenes systems of the present invention are shown. In FIG. 3, linear diazene chemical structure as both polymer and oligomeric extended patterns are illustrated. FIG. 4B illustrates an example of a linear chemical structure of the present invention including methoxy substituents. In FIG. 5 cyclic oligomer chemical structures of the present invention are shown. FIG. 6 illustrates a branched azo-triazine chemical structure of the present invention including hydrazine (NHNH$_2$) termini and FIG. 7 illustrates a branched azo-triazine of the present invention having aminoguanyl (NC(NH$_2$)(NHNH$_2$)) termini. Fused rings structures are shown in FIG. 8, particularly illustrating a linear extended azo-triazine structure of the present invention with fused. 1,2,3,5-tetrazinyl groups including =NH termini. Examples of N-oxide dendrimer and polymeric systems of the present invention are shown in FIGS. 9 and 10.

The triazinyl diazenes of the present invention are designed to incorporate features of high energy content, while also offering high density and stability due to their ability to form a planar network of substituted triazines linked through azo bonds. These propellant ingredients provide improved combustion by reducing the pressure exponent of rocket motors, due to the potential for formation of quantities of highly thermally stable cyclic azines during the combustion process (see e.g., T. Brill, Chemistry in Britain, 1993, No. 1, p. 36, the disclosure of which is herein incorporated by reference). The triazinyl diazene oligomers make up a versatile network having properties that may be modified by the nature of the triazine substituents. Representative substituents, such as hydrazinyl, may serve as a link to the binder by reactions with curing agents or directly with binders that contain groups reactive with amines, such as, epoxy groups or esters. The azo group may also function as a linkage site with binders by cycloaddition reactions. Cyclic oligomers of triazinyl diazenes may complex to binders through host-guest interactions with pendant binder groups, or may complex with the NH$_4^+$ of oxidizer salts by incorporation into the cavity of cyclic oligomers formed by hydrazo linkages of the triazines. These novel binder-filler interactions, involving cycloaddition and host-guest chemistry, may be tailored to permit curing of propellant mixes without the use of sensitive and reactive reagents. Additionally, the properties of the triazinyl diazenes may be optimized by varying the nature of the linkages, e.g., the degree of branching and the molecular weight of the oligomers, by the use of cyclic oligomers, which may also offer advantage as cryptands, and by the exploitation of appending groups to the triazine such as: tetrazolo, aminotetrazolo, nitrotriazolo, amino, hydrazino (and nitrate, perchloroate salts thereof). Furthermore, the triazine rings may be fused to rings such as: tetrazolo, 1, 2,4-triazolo, 1,2,4-triazolone, and 1,2,4-triazolimine.

In an embodiment, the present invention provides a new class of propellant ingredients based on the linkage of triazine heterocycles with azo groups. As seen below, a comparison of a tetra-hydrazino-diazene (labeled THAT) and dihydro-diazene (labeled DH-THAT) compounds are shown, having calculated values of ΔH$_f$ of 357 kcal/mol and ΔH$_f$ of 348 kcal/mol, respectively.

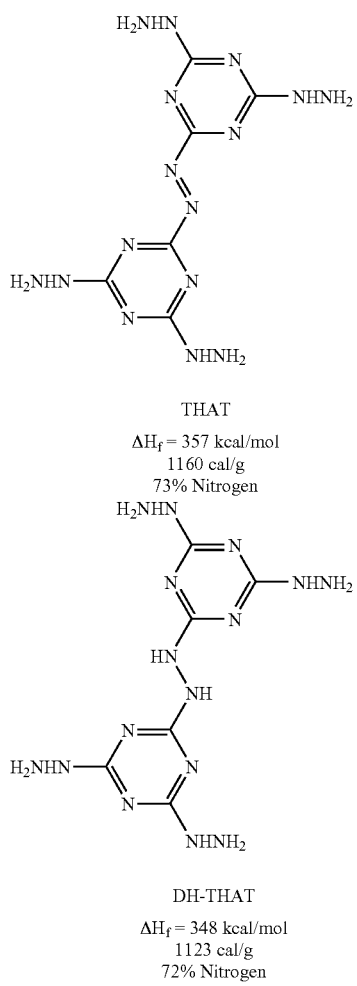

THAT

ΔH$_f$ = 357 kcal/mol
1160 cal/g
73% Nitrogen

DH-THAT

ΔH$_f$ = 348 kcal/mol
1123 cal/g
72% Nitrogen

In particular, these planar arrays of azo-coupled rings of the present invention are calculated to have energies from about 1300 cal/g to about 1600 cal/g, and more particularly from about 1300 cal/g to about 1450 cal/g, and an average composition of about $C_3H_3N_6$ to about $C_3H_3N_{20}$, such as $C_3H_3N_9$, etc., with such energies and composition resulting from selection of structure of the present invention including the pendent groups attached thereto. With increases in nitrogen content, such as at a level of 76% nitrogen, these materials are expected to produce a lower flame temperature during combustion. Most particularly, these high energy propellant ingredients are useful for anti-air weaponry, i.e., engagement of aerial threats, by improving the thrust of propellants in order to intercept missiles nearer their point of origin. In an embodiment, the extended azo-triazine systems of the present invention may be incorporated into nanoparticles.

In an embodiment, the azo-coupled 1,3,5-triazines of the present invention are created from a hydrazine group on the triazine that is sufficiently nucleophilic to displace chlorine from dimethoxy- and diamino-substituted, 2-chlorotriazines. The resultant hydrazo linkages are then oxidized to azo groups. Through this approach extended and dendritic azo-triazine systems can be constructed. When a triazine network is assembled, the terminal triazine rings, and the 1,3-coupled triazines in the extended network series, have the non-coupled carbons converted to C—NHNH$_2$ sites. This pure CHN network may be derivatized, in order to increase the energy content, by the formation of nitrate and perchlorate salts of the pendant hydrazine groups. The CHN system may also be transformed by peracid treatment to give N-oxide derivatives. These azo-coupled networks thus offer a platform for a variety of unique, high-energy CHN materials as well as a parallel series of more energetic CHNO compounds.

Oligomer structures of the present invention include a polymeric molecule having small numbers of monomer units, such as dimer, trimer, tetramer, etc. structures, with about 1 to about 10000 monomer units, including ranges, such as, from about 1 to about 5000, 1 to about 1000, 1 to about 500, 1 to about 100, 1 to about 50, etc. Dendritic structures include branching molecular structures of the present invention. The maximized dendritic growth in the 1,3,5-triazine system evolves from a central ring to give a structure with an average composition of (—N═N—)$_3$ (CN)$_3$. The extended type network can proceed from coupling at the 1,3-positions for an arbitrary length and then become dendritic, or continue as 1,3-coupling. These patterns are shown below in Illustration A, A (branched), B (linear) and C (dendritic), for arbitrary lengths, with the azo bond units represented as dashed double connections.

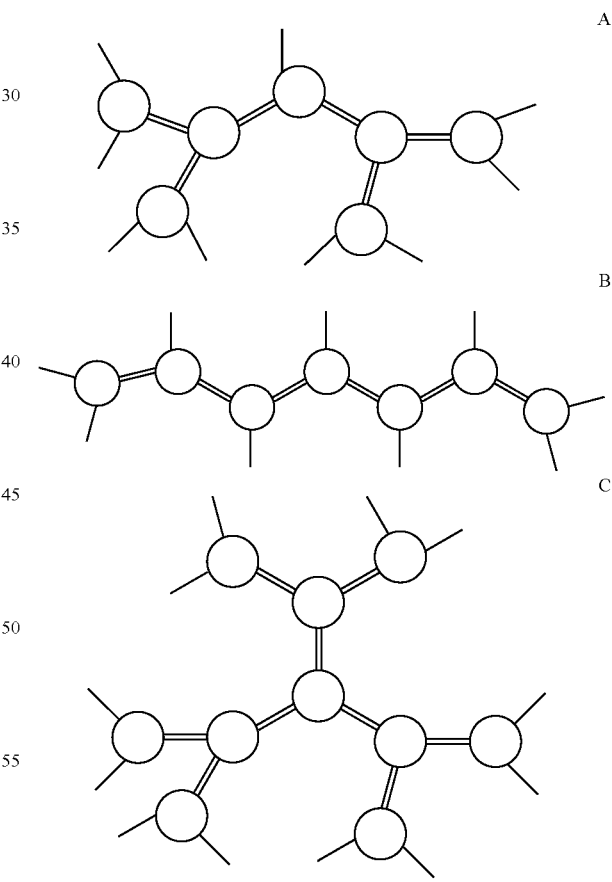

Illustration A

The present invention provides a novel class of dendritic energetics, in the form of azo-triazine oligomers, useful in high-energy propellant ingredients. These novel high energy propellant ingredients retain an insensitivity from a dense, layered molecular structure and a suppressed flame temperature due to high nitrogen content.

The foregoing summary, description, and examples of the present invention are not intended to be limiting, but are only exemplary of the inventive features which are defined in the claims.

Finally, any numerical parameters set forth in the specification and attached claims are approximations (for example, by using the term "about") that may vary depending upon the desired properties sought to be obtained by the present invention. At the very least, and not as an attempt to limit the application of the doctrine of equivalents to the scope of the claims, each numerical parameter should at least be construed in light of the number of significant digits and by applying ordinary rounding.

What is claimed is:

1. A compound of the chemical structure:

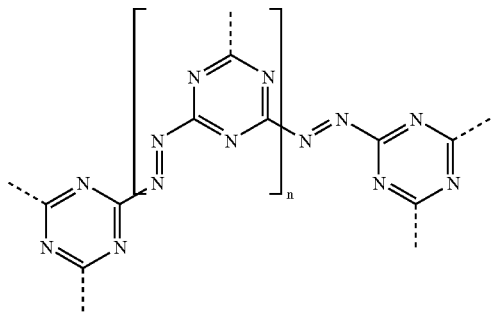

wherein n is greater than zero.

2. The compound of claim 1, wherein a the value of n is at least 1.

3. The compound of claim 1, wherein the value of n ranges from 1 to about 1,000.

4. A compound of the chemical structure:

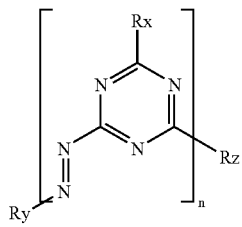

wherein Rx, Ry and Rz are individually selected from at least one member of a group of energetic components and non-energetic components,
   wherein n is greater than zero,
   wherein the chemical structure comprises a 1,3,5-triazine ring, said 1,3,5-triazine ring comprises at least two carbon atoms each adjacent to a —N=N— coupling where one of said at least two carbon atoms is azo coupled to an additional triazine ring, and
   wherein said non-energetic components are selected from a chlorine atom, a methoxy group and an amino group.

5. The compound of claim 4, wherein Ry is the

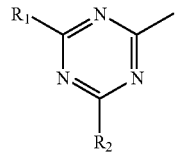

chemical structure:
   and, Rz

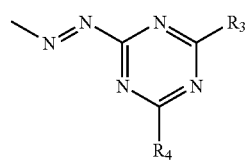

is the chemical structure:
   wherein Rx, $R_1$, $R_2$, $R_3$ and $R_4$ are each individually selected from an energetic substituent and a non-energetic substituent, and wherein said non-energetic substituent is selected from one of a chlorine atom, a methoxy group and an amino group.

6. The compound of claim 5, wherein at least one of Rx, $R_1$, $R_2$, $R_3$ and $R_4$, individually, is an energetic substituent.

7. The compound of claim 5, wherein at least one of Rx, $R_1$, $R_2$, $R_3$ and $R_4$, individually, is at least one member selected from $NC(NH_2)(HNNH_2)$, NH, $NH_2$, $NHNH_2$ and $NC(NH_2)_2$.

8. The compound of claim 5, wherein at least one of Rx, $R_1$, $R_2$, $R_3$ and $R_4$, individually, is $NC(NH_2)_2$.

9. The compound of claim 5, wherein at least one of Rx, $R_1$, $R_2$, $R_3$ and $R_4$, individually, is $NHNH_2$.

10. The compound of claim 5, wherein at least one of Rx, $R_1$, $R_2$, $R_3$ and $R_4$, individually, includes an oxygenated nitrogen component wherein the oxygenated nitrogen component is at least one member selected from the group consisting of —N→O and —N=N—O.

11. A linear azo-triazine consisting of the compound of claim 4.

12. A branched azo-triazine consisting of the compound of claim 4.

13. A dendritric azo-triazine consisting of the compound of claim 4.

14. An oligomer azo-triazine consisting of compound of claim 4.

15. A cyclic oligomer azo-triazine consisting of the compound of claim 4.

16. An energetic material comprising the compound of claim 4, wherein said energetic material is selected from the group consisting of propellants, pyrotechnics and high energy detonators.

17. A propellant comprising the energetic material of claim 16,
   wherein said non-energetic components are selected from a chlorine atom, a methoxy group and an amino group.

18. A process for producing azo-triazine compounds of claim 1, comprising:
   providing an N,N'-Bis-(4,6-disubstituted-[1,3,5]triazin-2-yl)hydrazine;
   forming a diazene form of said hydrazine; and,
   extending the formed diazene.

* * * * *

UNITED STATES PATENT AND TRADEMARK OFFICE
CERTIFICATE OF CORRECTION

| | |
|---|---|
| PATENT NO. | : 7,399,841 B1 |
| APPLICATION NO. | : 11/229429 |
| DATED | : July 15, 2008 |
| INVENTOR(S) | : William M. Koppes et al. |

Page 1 of 1

It is certified that error appears in the above-identified patent and that said Letters Patent is hereby corrected as shown below:

On the Title page, Item (75) Inventors, Line 4, one of the named inventors, should appear as follows:

Farhad Forohar

Signed and Sealed this

Seventeenth Day of August, 2010

David J. Kappos
*Director of the United States Patent and Trademark Office*